US010446871B2

(12) United States Patent
Chika

(10) Patent No.: US 10,446,871 B2
(45) Date of Patent: Oct. 15, 2019

(54) LITHIUM SALT COMPOUND, NONAQUEOUS ELECTROLYTE SOLUTION USING SAME, LITHIUM ION SECONDARY BATTERY AND LITHIUM ION CAPACITOR

(71) Applicant: UBE INDUSTRIES, LTD., Ube-shi (JP)

(72) Inventor: Junichi Chika, Ube (JP)

(73) Assignee: UBE INDUSTRIES, LTD., Ube-shi (JP)

( * ) Notice: Subject to any disclaimer, the term of this patent is extended or adjusted under 35 U.S.C. 154(b) by 9 days.

(21) Appl. No.: 15/572,969

(22) PCT Filed: Dec. 21, 2015

(86) PCT No.: PCT/JP2015/085697
§ 371 (c)(1),
(2) Date: Nov. 9, 2017

(87) PCT Pub. No.: WO2016/189769
PCT Pub. Date: Dec. 1, 2016

(65) Prior Publication Data
US 2018/0159173 A1 Jun. 7, 2018

(30) Foreign Application Priority Data
May 27, 2015 (JP) ................... 2015-107963

(51) Int. Cl.
| | |
|---|---|
| *H01M 6/14* | (2006.01) |
| *H01M 10/0525* | (2010.01) |
| *C07C 43/04* | (2006.01) |
| *C07F 9/06* | (2006.01) |
| *H01G 11/62* | (2013.01) |
| *H01M 10/0568* | (2010.01) |
| *H01M 10/0569* | (2010.01) |
| *H01G 11/64* | (2013.01) |
| *C01B 25/455* | (2006.01) |
| *C07F 1/02* | (2006.01) |
| *H01G 11/06* | (2013.01) |
| *H01G 11/60* | (2013.01) |

(52) U.S. Cl.
CPC ......... *H01M 10/0525* (2013.01); *C07C 43/04* (2013.01); *C07F 9/06* (2013.01); *H01G 11/62* (2013.01); *H01G 11/64* (2013.01); *H01M 10/0568* (2013.01); *H01M 10/0569* (2013.01); *C01B 25/455* (2013.01); *C07F 1/02* (2013.01); *H01G 11/06* (2013.01); *H01G 11/60* (2013.01); *H01M 2300/0034* (2013.01); *Y02E 60/13* (2013.01); *Y02P 70/54* (2015.11); *Y02T 10/7022* (2013.01)

(58) Field of Classification Search
CPC ........... H01M 10/0525; H01M 10/052; H01M 10/0568; H01M 10/0569; H01M 2300/0034; C07C 43/04; C07F 9/06; C07F 1/02; H01G 11/62; H01G 11/64; H01G 11/06; H01G 11/60; C01B 25/455; Y02E 60/13; Y02P 70/54; Y02T 10/7022
See application file for complete search history.

(56) References Cited

U.S. PATENT DOCUMENTS

| | | | |
|---|---|---|---|
| 8,283,074 B2 * | 10/2012 | Amine | H01G 9/038 252/62.2 |
| 2010/0323240 A1 | 12/2010 | Tsujioka et al. | |
| 2011/0177398 A1 | 7/2011 | Affinito et al. | |
| 2012/0107701 A1 | 5/2012 | Iwaya | |

(Continued)

FOREIGN PATENT DOCUMENTS

| | | |
|---|---|---|
| EP | 2 450 998 A1 | 5/2012 |
| JP | 10-291994 A | 11/1996 |
| JP | 11-67270 A | 3/1999 |

(Continued)

OTHER PUBLICATIONS

Extended European Search Report dated Dec. 10, 2018 in European Patent Application No. 15893401.8, 6 pages.
International Search Report dated Mar. 22, 2016, In PCT/JP2015/085697 filed Dec. 21, 2015.
Han et al., "Solvate Structures and Computational/Spectroscopic Characterization of $LiPF_6$ Electrolytes", The Journal of Physical Chemistry, vol. 119, (2015), pp. 8492-8500.

(Continued)

*Primary Examiner* — Raymond Alejandro
(74) *Attorney, Agent, or Firm* — Oblon, McClelland, Maier & Neustadt, L.L.P.

(57) ABSTRACT

The present invention is concerned with (1) a lithium salt compound including a lithium cation including, as a ligand, at least one ether compound selected from 2,5,8,11-tetraoxadodecane and 2,5,8,11,14-pentaoxapentadecane and a difluorophosphate anion; (2) a nonaqueous electrolytic solution having an electrolyte salt dissolved in a nonaqueous solvent, the nonaqueous electrolytic solution containing the aforementioned lithium salt compound; (3) a lithium ion secondary battery including a positive electrode, a negative electrode, and the aforementioned nonaqueous electrolytic solution; (4) a lithium ion capacitor using the aforementioned nonaqueous electrolytic solution; and (5) a production method of the aforementioned lithium salt compound, including bringing the aforementioned ether compound and lithium difluorophosphate into contact with each other. The nonaqueous electrolytic solution of the present invention is excellent in high-temperature cyclic property and output characteristics after high-temperature cycles and is capable of suppressing metal elution from a positive electrode or the like.

13 Claims, No Drawings

(56) References Cited

U.S. PATENT DOCUMENTS

2015/0064574 A1* 3/2015 He .................... H01M 10/0568
429/300

FOREIGN PATENT DOCUMENTS

| | | |
|---|---|---|
| JP | 2008-222484 A | 9/2008 |
| JP | 2008-277002 A | 11/2008 |
| JP | 2010-73489 A | 4/2010 |
| WO | WO 2011/136226 A1 | 11/2011 |

OTHER PUBLICATIONS

Hayamizu et al., nuclear magnetic resonance and ionic conductivity studies for liquid electrolytes composed of glymes and polystheneglycol dimethyl ethers of Journal of Chemical Physics, vol. 117, No. 12, (2002), pp. 5929-5939.

* cited by examiner

LITHIUM SALT COMPOUND, NONAQUEOUS ELECTROLYTE SOLUTION USING SAME, LITHIUM ION SECONDARY BATTERY AND LITHIUM ION CAPACITOR

TECHNICAL FIELD

The present invention relates to a novel lithium salt compound, a nonaqueous electrolytic solution using the same, and a lithium ion secondary battery and a lithium ion capacitor each using the nonaqueous electrolytic solution.

BACKGROUND ART

Attention has been paid recently to a power source for an automobile, such as an electric vehicle, a hybrid car, etc., and a lithium ion secondary battery and a lithium ion capacitor for idling stop.

As an electrolytic solution of a lithium secondary battery, a nonaqueous electrolytic solution in which an electrolyte, such as $LiPF_6$, $LiBF_4$, etc. is dissolved in a cyclic carbonate, such as ethylene carbonate, propylene carbonate, etc., and a linear carbonate, such as dimethyl carbonate, diethyl carbonate, ethyl methyl carbonate, etc., is used.

In order to improve battery characteristics of such a lithium secondary battery, such as load characteristics, cycle property, etc., various investigations regarding a nonaqueous solvent or an electrolyte salt to be used in such a nonaqueous electrolytic solution have been made.

NPL 1 proposes a complex salt having, as a ligand, an ether compound having a specified structure and reports that hard volatility is exhibited, and also proposes that the foregoing ether complex salt is formed into an electrolytic solution and utilized.

PTL 1 discloses an electrolytic solution using a complex electrolyte of a glyme, such as triethylene glycol dimethyl ether (triglyme), tetraethylene glycol dimethyl ether (tetraglyme), etc., with an alkali metal salt, such as lithium bis(trifluoromethanesulfonyl)imide (LiTFSI), etc., and a secondary battery and describes that thermal stability is high.

PTL 2 discloses a nonaqueous electrolytic solution secondary battery using a nonaqueous electrolytic solution containing lithium difluorophosphate and describes that the storage property is improved.

PTL 3 describes that an electrolytic solution containing a compound having a skeleton including a hetero element, the compound being a liquid at 25° C. and having a dielectric constant of 5 or more and a viscosity rate of 0.6 cP or less, such as dimethoxyethane, diethoxyethane, acetonitrile, etc., as well as lithium difluorophosphate ($LiPO_2F_2$) suppresses degradation of battery characteristics at the time of high-temperature storage.

In PTL 4, a nonaqueous electrolytic solution including lithium difluorophosphate is disclosed, and in Example 3 thereof, an example in which 4.6% by mass of lithium difluorophosphate was added is described.

CITATION LIST

Patent Literature

PTL 1: JP 2010-73489 A
PTL 2: JP 11-067270 A
PTL 3: JP 2008-277002 A
PTL 4: JP 2008-222484 A

Non-patent Literature

NPL 1: *Journal of Chemical Physics*, vol. 117, 5929 (2002)

DISCLOSURE OF INVENTION

Technical Problem

A problem of the present invention is to provide a novel lithium salt compound, a nonaqueous electrolytic solution using the same, which is excellent in high-temperature cycle property and output characteristics after high-temperature cycles and is capable of suppressing metal elution from a positive electrode or the like, and a lithium ion secondary battery and a lithium ion capacitor each using the nonaqueous electrolytic solution.

Solution to Problem

The present inventor made extensive and intensive investigations regarding the performances of the nonaqueous electrolytic solutions of the aforementioned conventional technologies. As a result, in the nonaqueous electrolytic solution secondary battery composed of only a glyme solvent and an alkali metal salt as described PTL 1, though the safety may be improved to some extent because of hard volatility, it became clear that as compared with a nonaqueous electrolytic solution having an electrolyte, such as $LiPF_6$, $LiBF_4$, etc., dissolved in a cyclic carbonate and a linear carbonate, the viscosity of the electrolytic solution is very high, and therefore, the effect against a problem of improving the cycle property cannot be substantially exhibited.

In addition, even in a nonaqueous electrolytic solution which is obtained by adding a complex salt of an equimolar mixture of triethylene glycol dimethyl ether (triglyme: 2,5,8,11-tetraoxadodecane) or tetraethylene glycol dimethyl ether (tetraglyme: 2,5,8,11,14-pentaoxapentadecane) and lithium bis(trifluoromethanesulfonyl)imide [$(CF_3SO_2)_2NLi$: LiTFSI] to a nonaqueous electrolytic solution composed of $LiPF_6$, a cyclic carbonate, and a linear carbonate, the viscosity of the electrolytic solution is reduced as compared with the nonaqueous electrolytic solution composed of only a glyme solvent and an alkali metal salt, it became clear that the effect against a problem of improving the cycle property and the output characteristics after cycles cannot be substantially exhibited.

In addition, PTL 1 describes that an oxygen moiety of the ether structure of the glyme is coordinated with an alkali metal ion in a ratio of 1/1, and a complex is formed in at least a part in the electrolytic solution. However, PTL 1 does not describe at all the use of lithium difluorophosphate as the lithium salt.

The nonaqueous electrolytic solution secondary battery of PTL 2 could not be satisfied with the point that the high-temperature cycle property is improved, thereby suppressing elution of a metal ion from a positive electrode. In addition, PTL 2 does not describe at all any combination of lithium difluorophosphate with an ether compound.

In PTL 3, though lithium difluorophosphate and short-chain dimethoxyethane or the like are mixed, a suitable mixing proportion is not described, and these are merely added for the purpose of decreasing the viscosity of the electrolytic solution.

In Example 3 of PTL 4, 4.6% by mass of lithium difluorophosphate is added in the nonaqueous electrolytic solution including a cyclic carbonate and a linear carbonate. But, according to this way, the lithium difluorophosphate cannot be uniformly completely dissolved.

In view of the aforementioned present circumstances, it order to solve the aforementioned problems, the present inventor made extensive and intensive investigations, and as a result thereof, have found a compound having much higher solubility in an electrolytic solution than the aforementioned lithium difluorophosphate through substitution of the lithium difluorophosphate with a lithium salt compound of the present invention, that is a novel complex.

In addition, they have found out that when the lithium salt compound of the present invention composed of a lithium cation including, as a ligand, at least one ether compound selected from 2,6,8,11-tetraoxadodecane and 2,5,8,11,14-pentaoxapentadecane, each of which is a relatively long-chain ether compound, and a difluorophosphate anion is contained in the nonaqueous electrolytic solution, high-temperature cycle property and output characteristics after high-temperature cycles are excellent, and metal elution from a positive electrode or the like is able to be suppressed, thereby leading to accomplishment of the present invention.

Specifically, the present invention provides the following (1) to (5).
(1) A lithium salt compound including a lithium cation including, as a ligand, at least one ether compound selected from 2,5,8,11-tetraoxadodecane and 2,5,8,11,14-pentaoxapentadecane and a difluorophosphate anion.
(2) A nonaqueous electrolytic solution having an electrolyte salt dissolved in a nonaqueous solvent, the nonaqueous electrolytic solution containing the lithium salt compound as set forth in the above item (1).
(3) A lithium ion secondary battery including a positive electrode, a negative electrode, and a nonaqueous electrolytic solution having an electrolyte salt dissolved in a nonaqueous solvent, the nonaqueous electrolytic solution being the nonaqueous electrolytic solution as set forth in the above item (2).
(4) A lithium ion capacitor using the nonaqueous electrolytic solution as set forth in the above item (2).
(5) A production method of the lithium salt compound as set forth in the above (1), including bringing at least one ether compound selected from 2,5,8,11-tetraoxadodecane and 2,5,8,11,14-pentaoxapentadecane and lithium difluorophosphate into contact with each other.

Advantageous Effects of Invention

In accordance with the present invention, it is possible to provide a novel lithium salt compound, a nonaqueous electrolytic solution using the same, which is excellent in high-temperature cycle property and output characteristics after high-temperature cycles and is capable of suppressing metal elution from a positive electrode or the like, and a lithium ion secondary battery and a lithium ion capacitor each using the nonaqueous electrolytic solution.

DESCRIPTION OF EMBODIMENTS

[Lithium Salt Compound]
The lithium salt compound of the present invention is composed of a lithium cation (A) (hereinafter also referred to simply as "lithium cation (A)") including, as a ligand, at least one ether compound selected from 2,5,8,11-tetraoxadodecane (hereinafter also referred to as "TOD") and 2,5,8, 11,14-pentaoxapentadecane (hereinafter also referred to "POP") and a difluorophosphate anion [(PO$_2$F$_2$)$^-$].

The lithium salt compound of the present invention is typically represented by the following general formula (1) or (2). In addition, the lithium cation (A) is represented by a left-side moiety of the general formula (1) or (2).

$$[Li_2(TOD)]^{2+}[(PO_2F_2)^-]_2 \quad (1)$$

$$[Li_2(POP)]^{2+}[(PO_2F_2)^-]_2 \quad (2)$$

The lithium salt compound of the present invention is a lithium salt compound composed of the lithium cation (A) including, as a ligand, at least one ether compound selected from TOD and POP and the difluorophosphate anion. This lithium salt compound is a solvate and a solvent separated ion pair. Accordingly, the lithium salt compound has such a property that it is hard to be electrochemically decomposed, as compared with a complex including an ether compound that is not coordinated in a lithium ion, for example, the lithium bis(trifluoromethanesulfonyl)imide-TOD complex or lithium bis(trifluoromethanesulfonyl)imide-POP complex as described in PTL 1.

When the ether compound to be used is a short-chain ether compound, such as dimethoxyethane or diethoxyethane, the effects as in the lithium salt compound of the present invention are not revealed.

In the lithium cation (A), a molar ratio of the ether compound (ligand: TOD and/or POP) to the lithium ion (Li$^+$) is preferably 0.1 or more, more preferably 0.15 or more, and still more preferably 0.25 or more, and preferably 0.7 or less, more preferably 0.6 or less, and still more preferably 0.55 or less. More specifically, the molar ratio is preferably from 0.1 to 0.7, more preferably from 0.15 to 0.6, still more preferably from 0.25 to 0.55, and most preferably 0.5.

[Production Method of Lithium Salt Compound]
A production method of the lithium salt compound of the present invention includes bringing at least one ether compound selected from 2,5,8,11-tetraoxadodecane (TOD) and 2,5,8,11,14-pentaoxapentadecane (POP) and lithium difluorophosphate into contact with each other.

The contact of the ether compound (TOD and/or POP) with lithium difluorophosphate may be performed by a method of mixing the both and allowing the mixture to react while stirring or the like.

In the production method of the present invention, the reaction can be performed without using a reaction solvent. Accordingly, the lithium salt compound can be produced industrially advantageously and efficiently.

In the aforementioned reaction, a molar ratio of the ether compound (TOD and/or POP) that is a ligand to the lithium ion (Li$^+$) is preferably 0.3 or more, more preferably 0.4 or more, and still more preferably 0.45 or more, and preferably 5 or less, more preferably 3 or less, still more preferably 2 or less, and yet still more preferably 1.5 or less. More specifically, the molar ratio is preferably from 0.3 to 5, more preferably from 0.4 to 3, still more preferably from 0.45 to 2, and especially preferably from 0.45 to 1.5.

When the reaction is performed in such a molar ratio, TOD and/POP and lithium difluorophosphate can be readily allowed to react with each other, and a purity of the desired lithium salt compound can be increased.

From the viewpoint of suppressing decomposition of the produced lithium salt compound, a contact temperature (reaction temperature) between the aforementioned ether compound and lithium difluorophosphate is preferably low within a range where the reaction proceeds. Specifically, the contact temperature is from −30 to 80° C., more preferably from −28 to 50° C., still more preferably from −25 to 20° C., and especially preferably from −24 to 10° C.

Although a reaction pressure is not particularly limited, it is preferably from normal pressure (atmospheric pressure) to 1 MPa, and more preferably from normal pressure (atmospheric pressure) to 0.3 MPa.

Although a reaction time is not particularly limited, too, it is typically from 1 hour to 5 days, preferably from 2 hours to 4 days, and more preferably from 3 hours to 3 days.

The resulting lithium salt compound may be isolated as a solid by performing drying under vacuum at room temperature or the like, and as needed, washing may be performed with an ether solvent, such as tert-butyl methyl ether, etc. before drying.

The lithium salt compound may be added with an organic solvent serving as an electrolytic solution component, such as methyl ethyl carbonate, dimethyl carbonate, etc., and directly utilized as a nonaqueous electrolytic solution to be used for a lithium ion secondary battery, a lithium ion capacitor, or the like, without being isolated as a solid.

As for the lithium salt compound that is obtained by the production method of the present invention, its structure may be confirmed by means of proton nuclear magnetic resonance spectrum ($^1$H-NMR), nuclear magnetic resonance spectrum of fluorine (19F-NMR), elemental analysis, or the like.

[Nonaqueous Electrolytic Solution]

The nonaqueous electrolytic solution of the present invention is a nonaqueous electrolytic solution having an electrolyte salt dissolved in a nonaqueous solvent, the nonaqueous electrolytic solution containing the lithium salt compound, which contains a lithium cation including, as a ligand, at least one ether compound selected from 2,5,8,11-tetraoxadodecane (TOD) and 2,5,8,11,14-pentaoxapentadecane (POP) and a difluorophosphate anion.

Although the reasons why the nonaqueous electrolytic solution of the present invention is excellent in high-temperature cycle property and output characteristics after high-temperature cycles and is capable of suppressing metal elution from a positive electrode or the like are not always elucidated yet, the following may be considered.

As described above, the compound that is included in the nonaqueous electrolytic solution of the present invention is a lithium salt compound composed of the lithium cation (A) including, as a ligand, at least one ether compound selected from TOD and POP and the difluorophosphate anion [$(PO_2F_2)^-$]. Here, the lithium cation (A) is hard to be electrochemically decomposed, as compared with ether compounds not coordinated in a lithium ion, and therefore, it may be considered that the lithium cation (A) can improve the cycle property. In addition, the difluorophosphate anion quickly reacts with an active site on the electrode, and therefore, it forms a firm solid electrolyte interphase (SEI film) which does not hinder permeation of the lithium ion. Accordingly, in a bis(trifluoromethanesulfonyl)imide ion [$(CF_3SO_2)_2N^-$] or the like, that is not the difluorophosphate anion, improving effects of high-temperature cycle property and output characteristics after high-temperature cycles are not obtained; whereas in the lithium salt compound composed of the lithium cation (A) and the difluorophosphate anion [$(PO_2F_2)^-$] according to the present invention, it may be considered that excellent high-temperature cycle property and output characteristics after high-temperature cycles can be revealed.

In the nonaqueous electrolytic solution of the present invention, the content of the lithium salt compound composed of the aforementioned lithium cation (A) and the difluorophosphate anion, which is contained in the nonaqueous electrolytic solution, is preferably from 0.1 to 10% by mass in the nonaqueous electrolytic solution. When the content is 10% by mass or less, there is less concern that a surface film is excessively formed on the electrode, so that the output characteristics after cycles are worsened, whereas when the content is 0.1% by mass or more, the formation of a surface film is satisfactory, and the high-temperature cycle property is enhanced, and hence, the aforementioned range is preferred. The content is more preferably 0.3% by mass or more, still more preferably 1% by mass or more, and especially preferably 1.7% by mass or more in the nonaqueous electrolytic solution. In addition, the upper limit thereof is more preferably 9% by mass or less, still more preferably 7% by mass or less, and especially preferably 5% by mass or less.

[Nonaqueous Solvent]

As the nonaqueous solvent that is used for the nonaqueous electrolytic solution of the present invention, there is suitably exemplified at least one of a cyclic carbonate and a linear ester. In order to synergistically improve electrochemical characteristics in a broad temperature range, particularly cycle property at a high temperature, output characteristics after cycles, etc., it is preferred that a linear ester is included, it is more preferred that a linear carbonate is included, and it is especially preferred that both a cyclic carbonate and a linear carbonate are included.

The term "linear ester" is used as a concept including a linear carbonate and a linear carboxylic acid ester.

As the cyclic carbonate, there is exemplified at least one selected from ethylene carbonate (EC), propylene carbonate (PC), 4-fluoro-1,3-dioxolan-2-one (FEC), and vinylene carbonate (VC).

As the combination of cyclic carbonates, a combination of EC and VC, a combination of EC and FEC, and a combination of PC and VC are especially preferred.

When the nonaqueous solvent includes ethylene carbonate and/or propylene carbonate, the stability of a surface film formed on the electrode is improved, and in the case of using an energy storage device at a high temperature and a high voltage, the cycle property, the output characteristics after cycles, and the effect for suppressing metal elution from a positive electrode or the like are improved, and hence, such is preferred.

The content of ethylene carbonate and/or propylene carbonate is preferably 3% by volume or more, more preferably 5% by volume or more, and still more preferably 7% by volume or more relative to the total volume of the nonaqueous solvent. In addition, an upper limit thereof is preferably 40% by volume or less, more preferably 35% by volume or less, and still more preferably 25% by volume or less.

As the linear ester, there are suitably exemplified an asymmetric linear carbonate, a symmetric linear carbonate, and an asymmetric ethoxy group-containing linear carboxylic acid ester.

The asymmetric linear carbonate is preferably one having a methyl group. Specifically, methyl ethyl carbonate (MEC), methyl propyl carbonate, and methyl isopropyl carbonate are preferred, and methyl ethyl carbonate (MEC) is more preferred.

The symmetric linear carbonate is preferably dimethyl carbonate (DMC) or diethyl carbonate (DEC), and the linear carboxylic acid ester is preferably ethyl acetate (EA) or ethyl propionate.

Among the aforementioned linear esters, a combination of methyl ethyl carbonate (MEC) and dimethyl carbonate (DMC), a combination of methyl ethyl carbonate (MEC) and ethyl acetate, and a combination of methyl ethyl carbonate (MEC), dimethyl carbonate (DMC), and ethyl acetate are more preferred.

Although the content of the linear ester is not particularly limited, it is preferred to use the linear carbonate in the content ranging from 60 to 90% by volume relative to the total volume of the nonaqueous solvent. When the content is 60% by volume or more, the viscosity of the nonaqueous electrolytic solution does not become excessively high, whereas when it is 90% by volume or less, there is less concern that an electroconductivity of the nonaqueous electrolytic solution is decreased to cause the electrochemical characteristics in a broad temperature range, particularly cycle property at a high temperature, output characteristics after cycles, etc., to be worsened, and hence, the aforementioned range is preferred.

A proportion of the volume occupied by ethyl acetate (EA) in the linear ester is preferably 1% by volume or more, more preferably 2% by volume or more, and still more preferably 3% by volume or more. An upper limit thereof is preferably 10% by volume or less, more preferably 8% by volume or less, and still more preferably 6% by volume or less.

The case of the aforementioned blending composition is preferred because the high-temperature cycle property and the output characteristics after high-temperature cycles are excellent, and the metal elution from a positive electrode or the like can be suppressed.

From the viewpoint of improvement of electrochemical characteristics in a broad temperature range, particularly at a high temperature, a proportion of the cyclic carbonate to the linear ester is preferably from 10/90 to 45/55, more preferably from 15/85 to 40/60, and still more preferably from 20/80 to 35/65 in terms of a volume ratio of [(cyclic carbonate)/(linear ester)].

(Additive)

In the nonaqueous electrolytic solution of the present invention, as an additive that may be used in combination with the lithium salt compound of the present invention, there is exemplified at least one selected from an $SO_2$ group-containing compound, an aromatic compound, a carbon-carbon triple bond-containing compound, a lithium-containing ionic compound, a cyclic acetal compound, and a phosphazene compound.

Among those, at least one selected from an $SO_2$ group-containing compound, a carbon-carbon triple bond-containing compound, a lithium-containing ionic compound, and a cyclic acetal compound is preferred.

As the SOY group-containing compound, its kind is not particularly limited so long as it is a compound having an "$SO_2$ group" in a molecule thereof. As specific examples thereof, there is suitably exemplified at least one selected from 1,3-propanesultone, 1,3-butanesultone, 2,4-butanesultone, 1,4-butanesultone, 1,3-propenesultone, 2,2-dioxide-1,2-oxathiolane-4-yl acetate, ethylene sulfate, propylene sulfate, butane-1,4-diyl dimethanesulfonate, methylene methanesulfonate, and so on. Among those, 1,3-propanesultone is more preferred.

As the aromatic compound, its kind is not particularly limited so long as it is a compound having a "benzene ring" in a molecule thereof. As specific examples thereof, there is suitably exemplified at least one selected from cyclohexylbenzene, tert-butylbenzene, tert-amylbenzene, biphenyl, terphenyl (including o-, m-, and p-forms), fluorobenzene, hexafluorobenzene, octafluorotoluene, pentafluorophenyl methanesulfonate, dimethyl 2-phenylphenyl phosphate, diethyl 2-phenylphenyl phosphate, methyl phenyl carbonate, ethyl phenyl carbonate, methyl 2-phenylphenyl carbonate, phenyl 2-phenylphenyl carbonate, and so on. Among those, cyclohexylbenzene is more preferred.

As the carbon-carbon triple bond-containing compound, its kind is not particularly limited so long as it is a compound having a "carbon-carbon triple bond" in a molecule thereof. As specific examples thereof, there is suitably exemplified at least one selected from methyl 2-propynyl carbonate, 2-propynyl methanesulfonate, 2-propynyl vinylsulfonate, di(2-propynyl) oxalate, ethynyl ethylene carbonate, 2-propynyl 2-oxo-1,3-dioxolane-4-carboxylate, 2-butyne-1,4-diyl dimethanesulfonate, and so on. Among those, 2-butyne-1,4-diyl dimethanesulfonate (same as 1,4-butynediol dimethanesulfonate) is more preferred.

As the lithium-containing ionic compound, its kind is not particularly limited so long as it is a compound having "lithium" as a cation species. As specific examples thereof, there is suitably exemplified at least one selected from lithium difluorophosphate, lithium fluorosulfonate, lithium difluorobis [oxalate-O,O']phosphate (LiPFO), lithium tetrafluoro[oxalate-O,O']phosphate, lithium bis[oxalate-O,O']borate (LiBOB), lithium difluoro[oxalate-O,O']borate, lithium methyl sulfate, lithium ethyl sulfate, lithium 2,2,2-trifluoroethyl sulfate, and so on. Two or more thereof may also be used. Among those, at least one selected from LiBOB and lithium methyl sulfate is more preferred.

As the cyclic acetal compound, its kind is not particularly limited so long as it is a compound having an "acetal group" in a molecule thereof. As specific examples thereof, there is suitably exemplified at least one selected from 1,3-dioxolane, 1,3-dioxane, 1,3,5-trioxane, and so on. Two or more thereof may also be used. Among those, 1,3-dioxane is more preferred.

As the phosphazene compound, its kind is not particularly limited so long as it is a compound having an "N=P—N group" in a molecule thereof. As specific examples thereof, there is suitably exemplified at least one selected from methoxypentafluorocyclotriphosphazene, ethoxypentafluorocyclotriphosphazene, phenoxypentafluorocyclotriphosphazene, ethoxyheptafluorocyclotetraphosphazene, dimethylaminopentafluorocyclotriphosphazene, diethylaminopentafluorocyclotriphosphazene, and so on. Among those, ethoxypentafluorocyclotriphosphazene is more preferred.

The content of the aforementioned $SO_2$ group-containing compound, aromatic compound, carbon-carbon triple bond-containing compound, lithium-containing ionic compound, cyclic acetal compound, or phosphazene compound is preferably from 0.001 to 5% by mass, respectively in the nonaqueous electrolytic solution. When the content falls within this range, the surface film is satisfactorily formed without becoming excessively thick, and the high-temperature cycle property and the output characteristics after high-temperature cycles are enhanced. The content is more preferably 0.01% by mass or more, and still more preferably 0.1% by mass or more, and the upper limit thereof is more preferably 3.5% by mass or less, and still more preferably 2.5% by mass or less, in the nonaqueous electrolytic solution.

The compound that is used in combination with the lithium salt compound of the present invention is preferably used in combination of two or more thereof. Among the combinations, a combination of a lithium-containing ionic compound with at least one selected from an $SO_2$ group-containing compound, an aromatic compound, a carbon-carbon triple bond-containing compound, a cyclic acetal compound, and a phosphazene compound is more preferably used.

From the viewpoint of improving an output of each of the lithium ion secondary battery and the lithium ion capacitor, a lower limit of the HF concentration included in the nonaqueous electrolytic solution of the present invention is preferably 1 ppm or more, and more preferably 2 ppm or more, and an upper limit of the HF concentration is preferably 50 ppm or less, more preferably 20 ppm or less, and still more preferably 8 ppm or less.

From the viewpoint of improving an output of each of the lithium ion secondary battery and the lithium ion capacitor, a lower limit of the alcohol content included in the nonaqueous electrolytic solution of the present invention is preferably 1 ppm or more, and more preferably 2 ppm or more, and an upper limit of the alcohol content is preferably 50 ppm or less, more preferably 20 ppm or less, and still more preferably 8 ppm or less.

[Electrolyte Salt]

As the electrolyte salt that is used in the present invention, a lithium salt is suitably exemplified.

As the lithium salt, at least one selected from $LiPF_6$, $LiBF_4$, $LiN(SO_2F)_2$, and $LiN(SO_2CF_3)_2$ is preferred, and $LiPF_6$ is more preferred.

In general, a concentration of the lithium salt is preferably 0.8 M or more, more preferably 1.0 M or more, and still more preferably 1.2 M or more relative to the aforementioned nonaqueous solvent. In addition, an upper limit thereof is preferably 1.6 M or less, more preferably 1.5 M or less, and still more preferably 1.4 M or less.

[Production of Nonaqueous Electrolytic Solution]

The nonaqueous electrolytic solution of the present invention can be, for example, obtained by a method of mixing the aforementioned nonaqueous solvent and adding the lithium salt compound composed of the aforementioned lithium cation (A) and difluorophosphate anion to the aforementioned electrolyte salt and the nonaqueous electrolytic solution.

At this time, the nonaqueous solvent to be used and the compounds to be added to the nonaqueous electrolytic solution are preferably purified in advance to decrease impurities as far as possible within a range where the productivity is not remarkably worsened.

The nonaqueous electrolytic solution of the present invention may be used in the following first and second energy storage devices, in which the nonaqueous electrolyte may be used not only in the form of a liquid but also in the form of a gel. Furthermore, the nonaqueous electrolytic solution of the present invention may also be used for a solid polymer electrolyte. Above all, the nonaqueous electrolytic solution is preferably used for the first energy storage device (i.e., for a lithium battery) or for the second energy storage device (i.e., for a lithium ion capacitor) each using a lithium salt as the electrolyte salt, more preferably used for a lithium battery, and still more preferably used for a lithium ion secondary battery.

[First Energy Storage Device (Lithium Ion Secondary Battery)]

The lithium ion secondary battery (hereinafter also referred to as "lithium secondary battery") of the present invention includes a positive electrode, a negative electrode, and the aforementioned nonaqueous electrolytic solution having an electrolyte salt dissolved in a nonaqueous solvent. Other constitutional members than the nonaqueous electrolytic solution, such as the positive electrode, the negative electrode, etc., may be used without being particularly limited.

For example, as a positive electrode active material for a lithium secondary battery, a complex metal oxide containing lithium and at least one selected from cobalt, manganese, and nickel is used. Such a positive electrode active material may be used solely or in combination of two or more thereof.

As such a lithium complex metal oxide, at least one selected from $LiCoO_2$, $LiCo_{1-x}M_xO_2$ (wherein M represents one or more elements selected from Sn, Mg, Fe, Ti, Al, Zr, Cr, V, Ga, Zn, and Cu, and $0.001 \le x \le 0.05$), $LiMn_2O_4$, $LiNiO_2$, $LiCo_{1-x}Ni_xO_2$ ($0.01<x<1$), $LiCo_{1/3}Ni_{1/3}Mn_{1/3}O_2$, $LiNi_{0.5}Mn_{0.3}Co_{0.2}Mn_{0.3}O_2$, $LiNi_{0.8}Mn_{0.1}Co_{0.1}O_2$, $LiNi_{0.8}Co_{0.15}Al_{0.05}O_2$, a solid solution of $Li_2MnO_8$ and $LiMO_2$ (wherein M represents a transition metal, such as Co, Ni, Mn, Fe, etc.), and $LiNi_{1/2}Mn_{3/2}O_4$ is suitably exemplified. In addition, these materials may be used as a combination, such as a combination of $LiCoO_2$ and $LiMn_2O_4$, a combination of $LiCoO_2$ and $LiNiO_2$, and a combination of $LiMn_2O_4$ and $LiNiO_2$.

Among those, a lithium complex metal oxide capable of being used at 4.4 V (a potential of the positive electrode based on Li is 4.5 V) or more, such as $LiCo_{1/3}Ni_{1/3}Mn_{1/3}O_2$, $LiNi_{0.5}Mn_{0.3}Co_{0.2}O_2$, $LiNi_{1/2}Mn_{3/2}O_4$, and a solid solution of $Li_2MnO_3$ and $LiMO_2$ (wherein M represents a transition metal, such as Co, Ni, Mn, Fe, etc.), is more preferred; and $LiNi_{0.5}Mn_{0.3}Co_{0.2}O_2$ and $LiNi_{1/2}Mn_{3/2}O_4$ each having a high content of Ni are especially preferred. In the case where a positive electrode including Ni or Mn is used, the amount of Ni or Mn which elutes as a metal ion from a positive electrode increases, decomposition of the electrolytic solution on a negative electrode is promoted due to a catalytic effect of Ni or Mn deposited on the negative electrode, and electrochemical characteristics, such as high-temperature cycle property, etc., are worsened. However, the energy storage device using the nonaqueous electrolytic solution of the present invention is preferred because worsening of electrochemical characteristics, such as cycle property particularly at a high temperature, output characteristics after cycles, etc., and metal elution from a positive electrode can be suppressed.

An electroconductive agent of the positive electrode is not particularly limited so long as it is an electron-conductive material that does not undergo chemical change. For example, there is exemplified at least one carbon material selected from graphites, such as natural graphite (e.g., flaky graphite, etc.), artificial graphite, etc.; carbon blacks, such as acetylene black, Ketjen black, channel black, furnace black, lamp black, thermal black, etc.; and carbon nanotubes. In addition, the graphite, the carbon black, and the carbon nanotube may also be appropriately mixed and used.

The amount of the electroconductive agent added to a positive electrode mixture is preferably 1 to 10% by mass, and more preferably 2 to 5% by mass.

The positive electrode may be produced in such a manner that the aforementioned positive electrode active material is mixed with an electroconductive agent, such as acetylene black, carbon black, etc., and a binder, such as polytetrafluoroethylene (PTFE), polyvinylidene fluoride (PVDF), a copolymer of styrene and butadiene (SBR), a copolymer of acrylonitrile and butadiene (NBR), carboxymethyl cellulose (CMC), an ethylene-propylene-diene terpolymer, etc., to which a high-boiling point solvent, such as 1-methyl-2-pyrrolidone, etc., is then added, followed by kneading to provide a positive electrode mixture, and the positive electrode mixture is applied onto a collector, such as an aluminum foil, a stainless steel-made lath plate, etc., dried, shaped under pressure, and then heat-treated in vacuum at a temperature of about 50° C. to 250° C. for about 2 hours.

A density of the positive electrode except for the collector is generally 1.5 g/cm or more, and for the purpose of further increasing a capacity of the battery the density is preferably 2 g/cm$^3$ or more, more preferably 3 g/cm$^3$ or more, and still more preferably 3.6 g/cm$^3$ or more. An upper limit thereof is preferably 4 g/cm$^3$ or less.

As a negative electrode active material for a lithium secondary battery, one or more selected from a lithium metal, a lithium alloy, a carbon material capable of absorbing and releasing lithium [e.g., graphitizable carbon, non-graphitizable carbon having a lattice (002) spacing of 0.37 nm or more, graphite having a lattice (002) spacing of 0.34 nm or less, etc.], tin (elemental substance), a tin compound, silicon (elemental substance), a silicon compound, a lithium titanate compound, such as $Li_4Ti_5O_{12}$, etc., may be used. A combination of graphite and silicon, or a combination of graphite and a silicon compound, is especially preferred.

In the case where a combination of graphite and silicon, or a combination of graphite and a silicon compound, is used as the negative electrode active material, the content of silicon and the silicon compound in the whole of the negative electrode active materials is preferably 1 to 45% by mass, and more preferably 2 to 15% by mass. When the content falls within the aforementioned range, the battery capacity can be increased while suppressing worsening of the electrochemical characteristics of the lithium secondary battery according to the present invention or an increase of the electrode thickness, and hence, such is preferred.

As other negative electrode active materials for a lithium secondary battery, an oxide including titanium is preferred, and a lithium titanate compound having a spinel structure, such as $Li_4Ti_5O_{12}$, etc., is more preferred. When an oxide including titanium as the negative electrode active material and the nonaqueous electrolytic solution of the present invention are used, the cycle property at a high temperature and the output characteristics after cycles of the lithium ion secondary battery can be much more improved, and hence, such is preferred.

When a carbon nanotube is used as an electroconductive aid, the aforementioned effects are much more easily exhibited, and hence, such is preferred.

A specific surface area of the oxide including titanium is preferably 4 m$^2$/g or more and 100 m$^2$/g or less, and an average particle diameter on a volume basis as determined by the laser diffraction and scattering method is preferably 0.1 µm or more and 50 µm or less.

The negative electrode may be produced in such a manner that the same electroconductive agent, binder, and high-boiling point solvent as in the production of the positive electrode as described above are used and kneaded to provide a negative electrode mixture, and the negative electrode mixture is then applied on a collector, such as a copper foil, etc., dried, shaped under pressure, and then heat-treated in vacuum at a temperature of about 50° C. to 250° C. for about 2 hours.

A density of the negative electrode except for the collector is generally 1.1 g/cm$^3$ or more, and for the purpose of further increasing a capacity of the battery, the density is preferably 1.6 g/cm$^3$ or more. An upper limit thereof is preferably 2 g/cm$^3$ or less.

Although a separator for battery is not particularly limited, a single-layered or laminated micro-porous film of a polyolefin, such as polypropylene, polyethylene, an ethylene-propylene copolymer, etc., a woven fabric, a nonwoven fabric, or the like may be used. The laminate of a polyolefin is preferably a laminate of polyethylene and polypropylene, and above all, a three-layered structure of polypropylene/polyethylene/polypropylene is more preferred.

A thickness of the separator is preferably 2 µm or more, more preferably 3 µm or more, and still more preferably 4 µm or more. In addition, an upper limit thereof is preferably 30 µm or less, more preferably 20 µm or less, and still more preferably 15 µm or less.

The structure of the lithium battery is not particularly limited, and a coin-type battery, a cylinder-type battery, a prismatic battery, a laminate-type battery, or the like may be applied.

The lithium secondary battery in the present invention has excellent electrochemical characteristics in a broad temperature range even when a final charging voltage is 4.2 V or more, particularly 4.3 V or more, and furthermore, the characteristics are favorable even at 4.4 V or more. A final discharging voltage may be generally 2.8 V or more, and furthermore 2.5 V or more, and the final discharging voltage of the lithium secondary battery in the present invention may be 2.0 V or more. An electric current value is not particularly limited, and in general, the battery may be used within a range of from 0.1 to 30 C. In addition, the lithium battery in the present invention may be charged and discharged at −40 to 100° C., and preferably −10 to 80° C.

In the present invention, as a countermeasure against the increase in the internal pressure of the lithium battery, there may also be adopted such a method that a safety valve is provided in a battery cap, or a cutout is provided in a component, such as a battery can, a gasket, etc. In addition, as a safety countermeasure for prevention of overcharging, a circuit cut-off mechanism capable of detecting the internal pressure of the battery to cut off the electric current may be provided in the battery cap.

[Second Energy Storage Device (Lithium Ion Capacitor)]

The second energy storage device of the present invention is an energy storage device including the nonaqueous electrolytic solution of the present invention and storing energy by utilizing intercalation of a lithium ion into a carbon material, such as graphite, etc., as the negative electrode. This energy storage device is called a lithium ion capacitor (LIC). As the positive electrode, there are suitably exemplified one utilizing an electric double layer between an active carbon electrode and an electrolytic solution, one utilizing a doping/dedoping reaction of a n-conjugated polymer electrode, and the like. The electrolytic solution includes at least a lithium salt, such as $LiPF_6$, etc.

In the lithium ion capacitor, by using, as the negative electrode material, lithium titanate or a carbon material in which a lithium ion is absorbed or doped in advance in place of the active carbon, a negative electrode potential may be kept lower than that of a usual electric double layer capacitor. For that reason, the range of a voltage used of the cell can be widened.

Using the nonaqueous electrolytic solution of the present invention, it is possible to provide a lithium ion capacitor that is excellent in high-temperature cycle property and output characteristics after high-temperature cycles.

EXAMPLES

Synthesis Example 1

Synthesis of Bis(difluorophosphoryl)(2,5,8,11-tetraoxadodecane)dilithium

In a 100-mL flask, 20.0 g (112 mmol) of 2,5,8,11-tetraoxadodecane and 12.0 g (111 mmol) of lithium difluorophosphate were charged. After stirring at room temperature for 3 hours, the resulting mixture was cooled to −20° C. After standing for 2 days, a deposit was filtered off, and a filtrate was washed with tert-butyl methyl ether. The resulting solid was dried under vacuum at room temperature to obtain 19.33 g of bis(difluorophosphoryl)(2,5,8,11-tetraoxadodecane)dilithium as a white solid (yield: 88.4%).

With respect to the obtained bis(difluorophosphoryl)(2,5,8,11-tetraoxadodecane)dilithium, its structure was confirmed through measurements of $^1$H-NMR, $^{19}$F-NMR, and elemental analysis. The results are shown below.

<$^1$H-NMR Measurement Results>
 $^1$H-NMR (400 MHz, CD$_3$CN): 3.55 to 3.60 (8H, m), 3.49 to 3.55 (4H, m), 3.33 (6H, s)

<$^{19}$F-NMR Measurement Results>
 $^{19}$F-NMR (376.5 MHz, CD$_3$CN): 84.60 (4F, d, J=928.2 Hz)

<Elemental Analysis Results>
 Anal. Calcd For C$_8$H$_{18}$F$_4$Li$_2$O$_8$P$_2$: C, 24.39; H, 4.60, Found: C, 24.05; H, 4.62

Synthesis Example 2

Synthesis of Bis(difluorophosphoryl)(2,5,8,11,14-pentaoxapentadecane)dilithium

In a 100-mL flask, 11.11 g (50 mmol) of 2,5,8,11,14-pentaoxapentadecane, 10.80 g (100 mmol) of lithium difluorophosphate, and 4.50 g of dimethyl carbonate were charged. After stirring at room temperature for 3.5 hours, the dimethyl carbonated was distilled off under reduced pressure at 50° C. for 3 hours, thereby obtaining 22.14 g of bis(difluorophosphoryl)(2,5,8,11,14-pentaoxapentadecane)dilithium as a colorless viscous liquid (yield: 100.0%).

With respect to the obtained bis(difluorophosphoryl)(2,5,8,11,14-pentaoxapentadecane)dilithium, its structure was confirmed through measurement of $^1$H-NMR. The results are shown below.

<$^1$H-NMR Measurement Results>
 $^1$H-NMR (400 MHz, CD$_3$CN): 3.61 to 3.57 (12H, m), 3.52 to 3.48 (4H, m), 3.32 (6H, s)

Examples 1 to 19 and Comparative Examples 1 to 4

[Production of Lithium Ion Secondary Battery]

94% by mass of LiNi$_{0.34}$Mn$_{0.33}$Co$_{0.33}$O$_2$ and 3% by mass of acetylene black (electroconductive agent) were mixed, and the mixture was then added to and mixed with a solution which had been prepared by dissolving 3% by mass of polyvinylidene fluoride (binder) in 1-methyl-2-pyrrolidone in advance, followed by mixing, thereby preparing a positive electrode mixture paste. This positive electrode mixture paste was applied onto both surfaces of an aluminum foil (collector), dried, and treated under pressure, followed by cutting into a predetermined size, thereby producing a positive electrode sheet in a belt-like form. A density of the positive electrode except for the collector was 3.6 g/cm$^3$.

5% by mass of SiO (negative electrode active material) and 90% by mass of artificial graphite (d$_{002}$=0.335 nm, negative electrode active material) were mixed, and the mixture was then added to and mixed with a solution which had been prepared by dissolving 5% by mass of polyvinylidene fluoride (binder) in 1-methyl-2-pyrrolidone in advance, thereby preparing a negative electrode mixture paste. This negative electrode mixture paste was applied onto both surfaces of a copper foil (collector), dried, and treated under pressure, followed by cutting into a predetermined size, thereby producing a negative electrode sheet in a belt-like form. A density of the negative electrode except for the collector was 1.55 g/cm$^3$.

This electrode sheet was used and analyzed by X-ray diffractometry. As a result, a ratio [I(110)/I(004)] of the peak intensity I(110) of the (110) plane to the peak intensity I(004) of the (004) plane of the graphite crystal was 0.1.

The above-obtained positive electrode sheet, a microporous polyethylene film-made separator, and the above-obtained negative electrode sheet were laminated in this order, and the laminate was wound up in a spiral form. This wound body was accommodated in a nickel-plated iron-made cylinder-type battery serving as a negative electrode terminal. Furthermore, a nonaqueous electrolytic solution having each of compositions shown in Tables 1 and 2 was injected, and a battery cap having a positive electrode terminal was caulked via a gasket, thereby producing a 18650 type cylinder-type battery. The positive electrode terminal was previously connected to the interior of the battery by using the positive electrode sheet and an aluminum-made lead tab, and a negative electrode can was previously connected to the interior of the battery by using the negative electrode sheet and a nickel-made lead tab.

[Evaluation of High-Temperature Cycle Property]

In a thermostatic chamber at 55° C., the cylinder-type battery produced by the aforementioned method was charged up to a final voltage of 4.25 V (a potential of the positive electrode based on Li is 4.35 V) with a constant current of 1 C and under a constant voltage for 3 hours and then discharged down to a discharge voltage of 3.0 V with a constant current of 1 C. This operation was defined by one cycle and repeated until reaching 300 cycles. A discharge capacity retention rate after cycles was determined according to the following equation, thereby evaluating the high-temperature cycle property.

Discharge capacity retention rate (%)={(Discharge capacity at 300th cycle)/(Discharge capacity at 1st cycle)}×100

[Evaluation of Output Characteristics after High-Temperature Cycles]

In a thermostatic chamber at 25° C., the cylinder-type battery after high-temperature cycles was charged up to a final voltage of 4.25 V with a constant current of 1 C and under a constant voltage for 3 hours and then discharged down to a discharge voltage of 3.0 V with a constant current of 1 C (1 C capacity). Thereafter, the resulting battery was charged up to a final voltage of 4.25 V with a constant current of 1 C and under a constant voltage for 3 hours and then discharged down to a final voltage of 3.0 V with a constant current of 5 C (5 C capacity). A capacity ratio thereof {(5 C capacity)/(1 C capacity)} was defined as the output characteristics after cycles.

As for the output characteristics after high-temperature cycles, relative output characteristics were evaluated on a basis when the output characteristics of Comparative Example 1 were defined as 100%.

[Evaluation of Metal Elution Amount after High-Temperature Cycles]

The metal elution amount after high-temperature cycles was determined by identifying an amount of a metal electrodeposited on the negative electrode. As for the amount of a metal electrodeposited on the negative electrode, a negative electrode sheet obtained by disassembling the cylinder-type battery after high-temperature cycles and washing was dissolved in an acid, and thereafter, the metal elution amount in a total amount of Ni, Mn, and Co was analyzed by the ICP (inductively coupled plasma) optical emission spectroscopy (with "SPS3520UV", manufactured by Hitachi High-Tech Science Corporation).

As for the metal elution amount, a relative metal elution amount was evaluated on a basis when the total metal elution amount of Ni, Mn, and Co of Comparative Example 1 was defined as 100%.

The production conditions and battery characteristics of battery are shown in Tables 1 to 5

In Tables 1 to 2, $Li_2(TOD)(PO_2F_2)_2$ is an abbreviation of bis(difluorophosphoryl)(2,5,8,11-tetraoxadodecane)dilithium; $Li_2(POP)(PO_2F_2)_2$ is an abbreviation of bis(difluorophosphoryl)(2,5,8,11,14-pentaoxapentadecane)dilithium; and $Li(G3)_1TFSI$ is an abbreviation of lithium bis(trifluoromethanesulfonyl)imide-2,5,8,11-tetraoxadodecane.

The same is also applicable to Tables 3 to 5.

TABLE 1

| | Composition of electrolyte salt | Lithium salt compound | | Results of high-temperature cycle test | | |
|---|---|---|---|---|---|---|
| | Composition of nonaqueous electrolytic solution (Volume ratio of solvent) | Kind | Content in nonaqueous electrolytic solution (% by mass) | Discharge capacity retention rate (%) | Output characteristics (%) | Metal elution amount (%) |
| Example 1 | 1.3M LiPF6 EC/DMC/MEC (20/60/20) | $Li_2(TOD)(PO_2F_2)_2$ | 3 | 73 | 130 | 71 |
| Example 2 | 1.3M LiPF6 EC/MEC (20/80) | | 3 | 70 | 125 | 72 |
| Example 3 | 1.3M LiPF6 EC/VC/DMC/MEC (19/1/60/20) | | 0.2 | 67 | 119 | 79 |
| Example 4 | 1.3M LiPF6 EC/VC/DMC/MEC (19/1/60/20) | | 1.5 | 74 | 129 | 70 |
| Example 5 | 1.3M LiPF6 EC/VC/DMC/MEC (19/1/60/20) | | 3 | 78 | 133 | 67 |
| Example 6 | 1.3M LiPF6 EC/VC/DMC/MEC (19/1/60/20) | | 6 | 77 | 130 | 65 |
| Example 7 | 1.3M LiPF6 EC/VC/DMC/MEC (19/1/60/20) | | 8 | 74 | 126 | 62 |
| Example 8 | 1.3M LiPF6 EC/VC/DMC/MEC (19/1/60/20) | $Li_2(POP)(PO_2F_2)_2$ | 3 | 76 | 131 | 68 |
| Comparative Example 1 | 1.3M LiPF6 EC/VC/DMC/MEC (19/1/60/20) | — | — | 61 | 100 | 100 |
| Comparative Example 2 | 1.3M LiPF6 EC/VC/DMC/MEC (19/1/60/20) | $LiPO_2F_2$ | 1 | 65 | 116 | 99 |
| Comparative Example 3 | 1.3M LiPF6 EC/VC/DMC/MEC (19/1/60/20) | $Li(G3)_1TFSI$ | 3 | 55 | 92 | 102 |
| Comparative Example 4 | 1.3M LiPF6 EC/VC/DMC/MEC/TOD (19/1/60/15/5) | — | — | 49 | 86 | 108 |

TABLE 2

| | Composition of electrolyte salt Composition of nonaqueous electrolytic solution (Volume ration of solvent) | Lithium salt compound | | Other additive (Content in nonaqueous electrolytic solution (% by mass)) | Results of high-temperature cycle test | | |
|---|---|---|---|---|---|---|---|
| | | Kind | Content in nonaqueous electrolytic solution (% by mass) | | Discharge capacity retention rate (%) | Output characteristics (%) | Metal elution amount (%) |
| Example 9 | 1.3M LiPF6 EC/VC/DMC/MEC (19/1/60/20) | $Li_2(TOD)(PO_2F_2)_2$ | 3 | 1,3-Propanesulfone (1) | 80 | 136 | 62 |
| Example 10 | 1.3M LiPF6 EC/VC/DMC/MEC (19/1/60/20) | | | 1,4-Butynediol dimethanesulfonate (1) | 82 | 135 | 60 |
| Example 11 | 0.8M LiPF6 + 0.5M LiFSI EC/VC/DMC/MEC (19/1/60/20) | | | LiBOB (1) | 84 | 140 | 65 |
| Example 12 | 1.3M LiPF6 EC/VC/DMC/MEC (19/1/60/20) | | | Cyclohexylbenzene (2) | 79 | 136 | 67 |
| Example 13 | 1.3M LiPF6 EC/VC/DMC/MEC/EA (19/1/60/15/5) | | | Ethoxypentafluorocyclotri-phosphazene (1) | 78 | 137 | 63 |
| Example 14 | 1.3M LiPF6 EC/VC/DMC/MEC (19/1/60/20) | | | Lithium methyl sulfate (1) | 83 | 144 | 61 |
| Example 15 | 1.3M LiPF6 EC/VC/DMC/MEC (19/1/60/20) | | | 1,3-Dioxane (0.1) | 81 | 139 | 62 |
| Example 16 | 1.3M LiPF6 EC/VC/DMC/MEC (19/1/60/20) | | | 1,3-Dioxane (1) | 82 | 141 | 69 |
| Example 17 | 1.3M LiPF6 EC/VC/DMC/MEC (19/1/60/20) | | | Ethylene sulfate (1) | 84 | 142 | 67 |
| Example 18 | 1.3M LiPF6 EC/VC/DMC/MEC (19/1/60/20) | | | Methyl phenyl carbonate (1) | 80 | 135 | 68 |
| Example 19 | 1.3M LiPF6 EC/VC/DMC/MEC (19/1/60/20) | | | Lithium fluorosulfonate (1) | 82 | 143 | 64 |

Example 20 and Comparative Example 5

A positive electrode sheet was produced by using $LiNi_{1/2}Mn_{3/2}O_4$ (positive electrode active material) in place of the positive electrode active material used in Example 5 and Comparative Example 1. 94% by mass of $LiNi_{1/2}Mn_{3/2}O_4$ coated with amorphous carbon and 3% by mass of acetylene black (electroconductive agent) were mixed, and the mixture was then added to and mixed with a solution which had been prepared by dissolving 3% by mass of polyvinylidene fluoride (binder) in 1-methyl-2-pyrrolidone in advance, thereby preparing a positive electrode mixture paste.

A cylinder-type battery was produced and subjected to battery evaluation in the same manners as in Example 1 and Comparative Example 1, except that this positive electrode mixture paste was applied onto one surface of an aluminum foil (collector), dried, and treated under pressure, followed by cutting into a predetermined size; that in evaluating the battery, the final charging voltage and the final discharging voltage were set to 4.9 V and 2.7 V, respectively; and that the composition of the nonaqueous electrolytic solution was changed to a predetermined composition.

The metal elution amount was determined on a basis when the metal elution amount of Comparative Example 5 was defined as 100%.

The results are shown in Table 3.

TABLE 3

| | Composition of electrolyte salt Composition of nonaqueous electrolytic solution (Volume ratio of solvent) | Lithium salt compound | | Results of high-temperature cycle test | | |
|---|---|---|---|---|---|---|
| | | Kind | Content in nonaqueous electrolytic solution (% by mass) | Discharge capacity retention rate (%) | Output characteristics (%) | Metal elution amount (%) |
| Example 20 | 1.3M LiPF6 EC/FEC/MEC/DMC (10/10/60/20) | $Li_2(TOD)(PO_2F_2)_2$ | 3 | 72 | 125 | 78 |
| Comparative Example 5 | 1.3M LiPF6 EC/FEC/MEC/DMC (10/10/60/20) | — | — | 45 | 100 | 100 |

Example 21 and Comparative Example 6

A negative electrode sheet was produced by using lithium titanate ($Li_4Ti_5O_{12}$; negative electrode active material) in place of the negative electrode active material used in Example 5 and Comparative Example 1.

90% by mass of lithium titanate, 4% by mass of acetylene black (electroconductive agent), and 1% by mass of a carbon nanotube (electroconductive agent) were mixed, and the mixture was then added to and mixed with a solution which had been prepared by dissolving 5% by mass of polyvinylidene fluoride (binder) in 1-methyl-2-pyrrolidone in advance, thereby preparing a negative electrode mixture paste.

A cylinder-type battery was produced and subjected to battery evaluation in the same manners as in Example 1 and Comparative Example 1, except that this negative electrode mixture paste was applied onto a copper foil (collector), dried, and treated under pressure, followed by cutting into a predetermined size, thereby producing a negative electrode sheet; that in evaluating the battery, the final charging voltage and the final discharging voltage were set to 2.8 V and 1.2 V, respectively; and that the composition of the nonaqueous electrolytic solution was changed to a predetermined composition.

The results are shown in Table 4.

All of the lithium secondary batteries of Examples 1 to 19 each using the nonaqueous electrolytic solution including a lithium salt compound composed of a lithium cation including, as a ligand, a specified ether compound and a difluorophosphate anion are improved with respect to the high-temperature cycle property, the output characteristics after high-temperature cycles, and the effect for suppressing metal elution from a positive electrode, as compared with the lithium secondary batteries of Comparative Examples 1 to 4.

In addition, from comparison of Example 20 with Comparative Example 5 and comparison of Example 21 with Comparative Example 6, in the case of using $LiNi_{1/2}Mn_{3/2}O_4$ for the positive electrode, or in the case of using lithium titanate for the negative electrode, the same effects

TABLE 4

| | Composition of electrolyte salt | Lithium salt compound | | Results of high-temperature cycle test | | |
|---|---|---|---|---|---|---|
| | Composition of nonaqueous electrolytic solution (Volume ratio of solvent) | Kind | Content in nonaqueous electrolytic solution (% by mass) | Discharge capacity retention rate (%) | Output characteristics (%) | Metal elution amount (%) |
| Example 21 | 1.3M LiPF6 PC/DEC (30/70) | $Li_2(TOD)(PO_2F_2)_2$ | 3 | 89 | 150 | 67 |
| Comparative Example 6 | 1.3M LiPF6 PC/DEC (30/70) | — | — | 73 | 100 | 100 |

Examples 22 to 24 and Comparative Example 7

[Solubility Test]

A predetermined amount of bis(difluorophosphoryl)(2,5,8,11-tetraoxadodecane)dilithium obtained in the same production method as in Synthesis Example 1 was added to 50 g of the nonaqueous electrolytic solution used in Comparative Example 1, and the mixture was stirred at 25° C. for 10 minutes (Examples 22 to 24).

0.75 g of lithium difluorophosphate was added to 50 g of the nonaqueous electrolytic solution used in Comparative Example 1, and the mixture was stirred at 25° C. for 10 minutes (Comparative Example 7).

After stirring, in the case where a completely uniform liquid was obtained without causing an undissolved residue, the solubility was designated as "A", and in the case where an undissolved residue was found, the solubility was designated as "B". The results are shown in Table 5.

are brought, and therefore, it is clear that such effects are not an effect replying upon a specified positive electrode or negative electrode.

Furthermore, from comparison of Examples 22 to 24 with Comparative Example 7, it is noted that the lithium salt compound composed of a lithium cation including, as a ligand, an ether compound and a difluorophosphate anion is remarkably improved with respect to the solubility, as compared with lithium difluorophosphate.

The nonaqueous electrolytic solution of the present invention also has an effect for improving the high-temperature cycle property, the output characteristics after high-temperature cycles, and the like, as a nonaqueous electrolytic solution for energy storage device, such as lithium ion capacitor, etc.

INDUSTRIAL APPLICABILITY

When the nonaqueous electrolytic solution of the present invention is used, it is possible to obtain an energy storage device which is excellent in high-temperature cycle property and output characteristics after high-temperature cycles and is capable of suppressing metal elution from a positive electrode or the like. In particular, when the nonaqueous electrolytic solution of the present invention is used as a nonaqueous electrolytic solution for an energy storage device, such as a lithium secondary battery, a lithium ion capacitor, etc., to be mounted on an instrument having high possibility to be used at a high temperature, such as a hybrid electric vehicle, a plug-in hybrid electric vehicle, a battery electric vehicle, a tablet device, an ultrabook, etc., it is possible to obtain an energy storage device which is excellent in high-temperature cycle property and output characteristics after high-temperature cycles and is capable of suppressing metal elution from a positive electrode or the like.

TABLE 5

| | Lithium salt compound | | Results of solubility test | |
|---|---|---|---|---|
| | Kind | Addition amount to 50 g of nonaqueous electrolytic solution (g) | LiPO2F2 content in nonaqueous electrolytic solution (% by mass) | Solubility |
| Example 22 | $Li_2(TOD)(PO_2F_2)_2$ | 2.75 | 1.5 | A |
| Example 23 | | 5.50 | 3.0 | A |
| Example 24 | $Li_2(POP)(PO_2F_2)_2$ | 6.09 | 3.0 | A |
| Comparative Example 7 | $LiPO_2F_2$ | 0.75 | 1.5 | B |

The invention claimed is:

1. A nonaqueous electrolytic solution having an electrolyte salt dissolved in a nonaqueous solvent, the nonaqueous electrolytic solution comprising a lithium salt compound comprising a lithium cation including, as a ligand, at least one ether compound selected from 2,5,8,11-tetraoxadodecane and 2,5,8,11,14-pentaoxapentadecane and a difluorophosphate anion,
wherein, in the lithium cation, a molar ratio of the ether compound to a lithium ion ($Li^+$) is from 0.25-0.55;
wherein the lithium salt compound is bis(difluorophosphoryl)(2,5,8,11-tetraoxadodecane) dilithium or bis(difluorophosphoryl)(2,5,8,11,14-pentaoxapentadecane) dilithium: and
wherein a content of the lithium salt compound in the nonaqueous electrolytic solution is from 0.1 to 10% by mass.

2. The nonaqueous electrolytic solution according to claim 1, wherein a content of the lithium salt compound in the nonaqueous electrolytic solution is from 0.2 to 8% by mass.

3. The nonaqueous electrolytic solution according to claim 1, further comprising, as an additive, at least one selected from the group consisting an $SO_2$ group-containing compound, an aromatic compound, a carbon-carbon triple bond-containing compound, a lithium-containing ionic compound, a cyclic acetal compound, and a phosphazene compound.

4. The nonaqueous electrolytic solution according to claim 3, wherein the additive is at least one selected from ala $SO_2$ group-containing compound, a carbon-carbon triple bond-containing compound, a lithium-containing ionic compound, and a cyclic acetal compound.

5. The nonaqueous electrolytic solution according to claim 3, wherein the content of the additive in the nonaqueous electrolytic solution is from 0.001 to 5% by mass.

6. The nonaqueous electrolytic solution according to claim 1, comprising a nonaqueous solvent comprising at least one selected from a cyclic carbonate and a linear carbonate.

7. The nonaqueous electrolytic solution according to claim 4, wherein the additive is at least one $SO_2$ group-containing compound selected from the group consisting of 1,3-propanesultone, 1,3-butanesultone, 2,4-butanesultone, 1,4-butanesultone, 1,3-propenesultone, 2,2-dioxide-1,2-oxathiolane-4-yl acetate, ethylene sulfate, propylene sulfate, butane-1,4-diyl dimethanesulfonate, and methylene methanesulfonate.

8. The nonaqueous electrolytic solution according to claim 4, wherein the additive is at least one carbon-carbon triple bond-containing compound selected from the group consisting of methyl 2-propynyl carbonate, 2-propynyl methanesulfonate, 2-propynyl vinylsulfonate, di(2-propynyl) oxalate, ethynyl ethylene carbonate, 2-propynyl 2-oxo-1,3-dioxolane-4-carboxylate, and 2-butyne-1,4-diyl dimethanesulfonate.

9. The nonaqueous electrolytic solution according to claim 4, wherein the additive is at least one lithium-containing ionic compound selected from the group consisting of lithium difluorophosphate, lithium fluorosulfonate, lithium difluorobis[oxalate-O,O']phosphate, lithium tetrafluoro[oxalate-O,O']phosphate, lithium bis[oxalate-O,O']borate, lithium difluoro[oxalate-O,O']borate, lithium methyl sulfate, lithium ethyl sulfate, and lithium 2,2,2-trifluoroethyl sulfate.

10. The nonaqueous electrolytic solution according to claim 4, wherein the additive is at least one cyclic acetal compound selected from the group consisting of 1.3-dioxolane, 1,3-dioxane, and 1,3,5-trioxane.

11. A lithium ion secondary battery, comprising:
a positive electrode;
a negative electrode; and
a nonaqueous electrolytic solution having an electrolyte salt dissolved in a nonaqueous solvent, the nonaqueous electrolytic solution being the nonaqueous electrolytic solution according to claim 1.

12. The lithium ion secondary battery according to claim 11, wherein the negative electrode comprises, as a negative electrode active material, one or more selected from the group consisting of a lithium metal, a lithium alloy, a carbon material capable of absorbing and releasing lithium, tin, a tin compound, silicon, a silicon compound, and a lithium titanate compound.

13. A lithium ion capacitor comprising the nonaqueous electrolytic solution according to claim 1.

* * * * *